(12) United States Patent
Stoffaneller et al.

(10) Patent No.: US 8,571,673 B2
(45) Date of Patent: Oct. 29, 2013

(54) ENERGY SAVING SILENT MODE FOR HEARING IMPLANT SYSTEMS

(75) Inventors: Martin Stoffaneller, Innsbruck (AT); Martin J. Kerber, Innsbruck (AT)

(73) Assignee: MED-EL Elektromedizinische Geraete GmbH, Innsbruck (AU)

( * ) Notice: Subject to any disclaimer, the term of this patent is extended or adjusted under 35 U.S.C. 154(b) by 216 days.

(21) Appl. No.: 13/050,017

(22) Filed: Mar. 17, 2011

(65) Prior Publication Data
US 2011/0213444 A1    Sep. 1, 2011

Related U.S. Application Data

(63) Continuation-in-part of application No. 12/029,051, filed on Feb. 11, 2008, now abandoned.

(60) Provisional application No. 60/889,322, filed on Feb. 12, 2007, provisional application No. 61/314,664, filed on Mar. 17, 2010.

(51) Int. Cl.
   *A61N 1/05*    (2006.01)
(52) U.S. Cl.
   USPC ........................................... 607/55; 607/137
(58) Field of Classification Search
   USPC .................................................... 607/55, 137
   See application file for complete search history.

(56) References Cited

U.S. PATENT DOCUMENTS

| | | | |
|---|---|---|---|
| 5,012,520 A | 4/1991 | Steeger | 381/68 |
| 5,794,187 A | 8/1998 | Franklin et al. | 704/225 |
| 6,198,971 B1 | 3/2001 | Leysieffer | 607/55 |
| 2002/0055779 A1 | 5/2002 | Andrews | 623/11.11 |
| 2003/0082507 A1 | 5/2003 | Stypulkowski | 434/262 |
| 2004/0049242 A1* | 3/2004 | Ibrahim | 607/57 |
| 2004/0082985 A1* | 4/2004 | Faltys et al. | 607/116 |
| 2007/0121975 A1 | 5/2007 | Sacha et al. | 381/312 |

FOREIGN PATENT DOCUMENTS

| EP | 1398995 A2 | 3/2004 |
|---|---|---|
| WO | WO 98/02969 | 1/1998 |

OTHER PUBLICATIONS

European Patent Office, Officer Ivaylo Koprinarov, International Search Report and Written Opinion, PCT/US2008/053557, date of mailing Jul. 14, 2008, 12 pages.

* cited by examiner

*Primary Examiner* — Joseph Dietrich
(74) *Attorney, Agent, or Firm* — Sunstein Kann Murphy & Timbers LLP

(57) ABSTRACT

A signal processing arrangement for a cochlear implant system is described. A sensing microphone senses an acoustic signal to generate a corresponding electrical sound signal. An information detection circuit performs spectral analysis on the sound signal to identify the presence of speech information. A sound signal processing circuit generates an implant communications signal for the cochlear implant system based on the sound signal, and has an energy saving operational mode wherein the implant communications signal is generated only when the information detection circuit identifies that speech information is present in the sound signal.

25 Claims, 6 Drawing Sheets

ENERGY SAVING SILENT MODE FOR HEARING IMPLANT SYSTEMS

This application is a continuation-in-part of U.S. patent application Ser. No. 12/029,051, filed Feb. 11, 2008, now abandoned, which in turn claimed priority from expired U.S. Provisional Patent Application 60/889,322, filed Feb. 12, 2007, and this application also claims priority to expired U.S. Provisional Patent Application 61/314,664, filed Mar. 17, 2010, all of which are incorporated herein by reference.

FIELD OF THE INVENTION

The present invention relates to cochlear implant systems, and more specifically to power management in such systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processor 111 which implements one of various known signal processing schemes. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing. The processed signal is converted by the external signal processor 111 into a digital data format, such as a sequence of data frames, for transmission into a receiving stimulator processor 108. Besides extracting the audio information, the receiver processor in the stimulator processor 108 may perform additional signal processing such as error correction, pulse formation, etc., and produces a stimulation pattern (based on the extracted audio information) that is sent through electrode lead 109 to an implanted electrode array 110. Typically, the electrode array 110 includes multiple stimulation contacts on its surface that provide selective electrical stimulation of the cochlea 104.

Besides getting the processed audio information to the implanted stimulator processor 108, existing cochlear implant systems also need to deliver electrical power from outside the body through the skin to satisfy the power requirements of the implanted portion of the system. FIG. 1 shows an arrangement based on inductive coupling through the skin to transfer both the required electrical power and the processed audio information. As shown in FIG. 1, a primary transmitter coil 107 (coupled to the external signal processor 111) is externally placed on the patient's skin adjacent to a subcutaneous secondary receiving coil in the stimulator processor 108. This arrangement inductively couples a radio frequency (rf) electrical signal to the stimulator processor 108 which is able to extract both a power component from the rf signal it receives, and the audio information for the implanted portion of the system.

The power component is extracted and stored in one or more (rechargeable) batteries, for example, in the stimulator processor 108. The current consumption supplied from the implanted batteries to the implanted components is an important system factor. In relative terms, the amount of current drawn from the batteries by the implanted components is very high and contributes to the end of battery lifetime. In contrast, low current consumption increases the number of (de)charging cycles which directly increases battery lifetime. Especially for fully implantable cochlear implants, low current consumption is important because the end of battery lifetime requires a surgical operation that bears many of the risks known with CI implantation.

SUMMARY OF THE INVENTION

Embodiments of the present invention are directed to a signal processing method and arrangement for a cochlear implant system. A sensing microphone senses an acoustic signal to generate a corresponding electrical sound signal. An information detection circuit performs spectral analysis on the sound signal to identify the presence of speech information. A sound signal processing circuit generates an implant communications signal for the cochlear implant system based on the sound signal, and has an energy saving operational mode wherein the implant communications signal is generated only when the information detection circuit identifies that speech information is present in the sound signal.

In further specific embodiments, the energy saving operational mode may be controlled based on a hysteresis threshold, which may be software programmable and/or user controllable. The arrangement may also include a minimum operational time requirement for which the sound signal processing circuit is enabled by the information detection circuit. And the information detection circuit may include a voice activation detections (VAD) circuit using a windowed spectral power analysis approach.

There also may be a signal delay memory for providing a processing delay to avoid loss of speech information around the time when the information detection circuit initially identifies that speech information is present in the sound signal. This may be in parallel with information detection circuit, and the sound signal processing circuit also may be in parallel with the information detection circuit and in series with the signal delay memory. And there may be a memory control switch between the sound signal processing circuit and the signal delay memory for controlling whether the implant communications signal passes through or bypasses the signal delay memory. In some embodiments, there may be a direct signal path in parallel with the information detection circuit and the signal delay memory for coupling the sound signal directly to the sound signal processing circuit without delay, in which case, there may or may not also be a memory control switch in series with the direct signal path and the signal delay memory for controlling whether the sound signal passes through the direct signal path or the signal delay memory.

DETAILED DESCRIPTION OF SPECIFIC EMBODIMENTS

Figure 1:
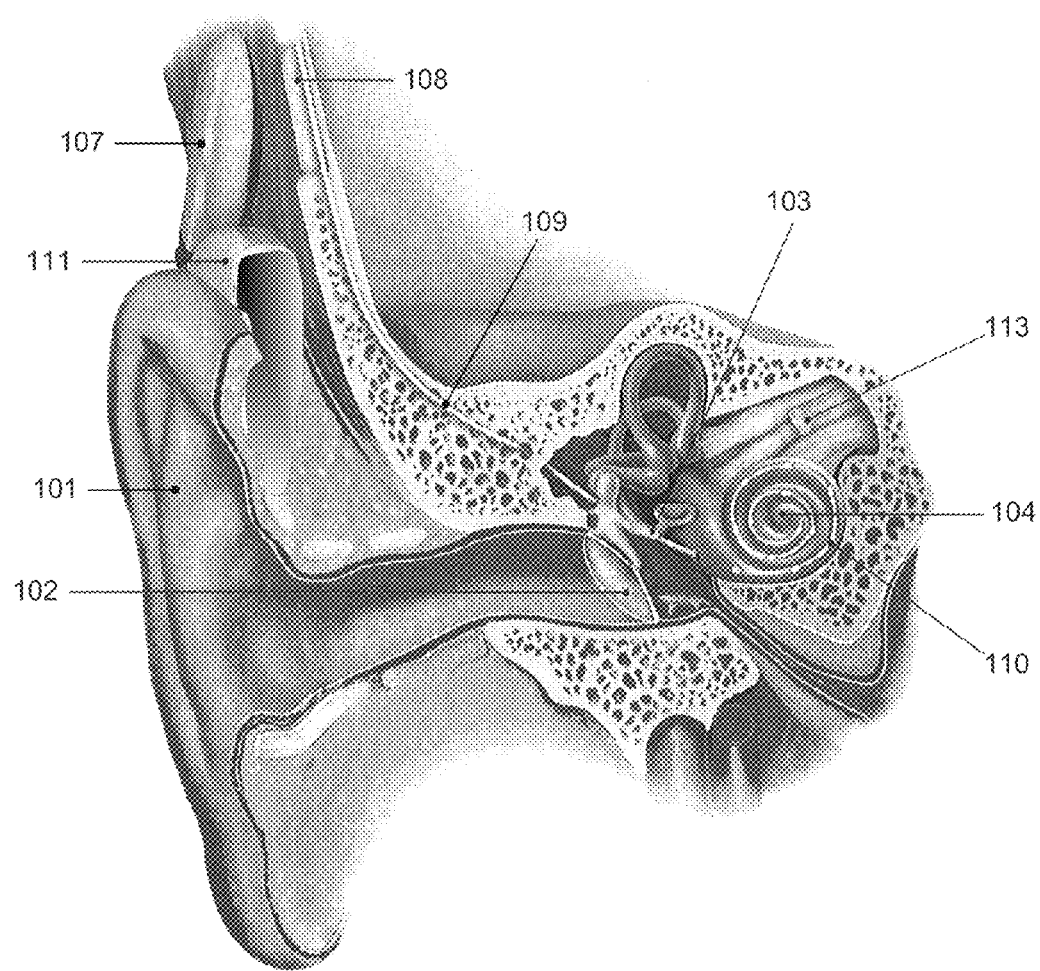
FIG. 1 shows anatomical features of a typical human ear having a cochlear implant system.
Figure 2:
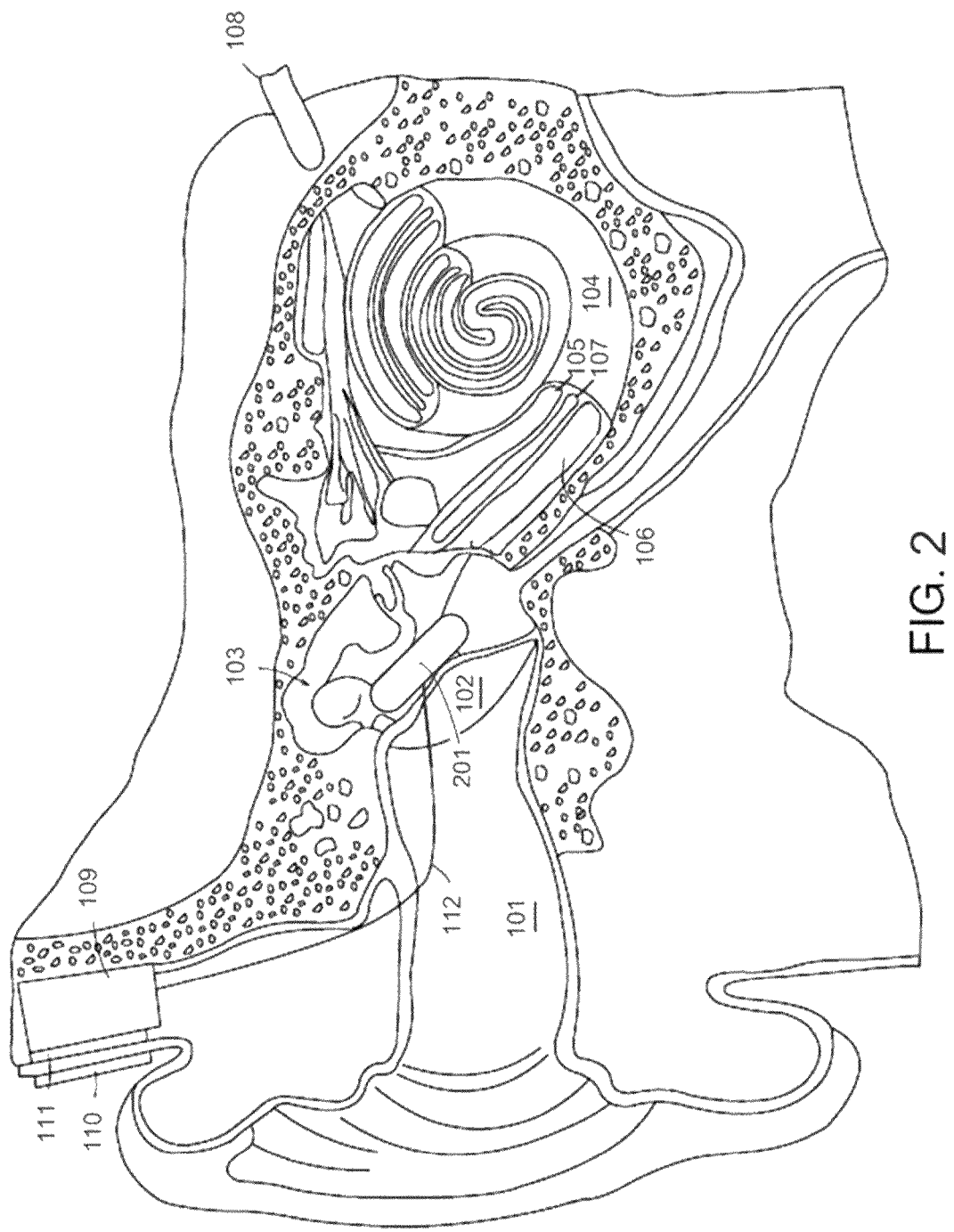
FIG. 2 illustrates a section view of an ear connected to a middle ear implant system according to an embodiment of the present invention.

In the cochlear implant system shown in FIG. 1, the stimulator processor 108 may include a sensing microphone which detects acoustic activity across the nearby skin boundary. FIG. 2 illustrates a section view of an ear connected to a middle ear implant system which has a middle ear stimulator 201 instead of an electrode carrier as in a cochlear implant system. The middle ear stimulator 201 mechanically drives the ossicular chain, which in turn stimulates the cochlea 104. A middle ear implant based on a floating mass transducer is described, for example, in U.S. Pat. Nos. 5,913,815; 5,897, 486; 5,624,376; 5,554,096; 5,456,654; 5,800,336; 5,857,958; and 6,475,134, each of which is incorporated herein by reference. But again, such a system may have an implanted sensing microphone incorporated into the housing of the receiver processor 109.

One problem with an implanted microphone is that the electric signal it generates can be affected by other noises than simply the acoustic environment near the patient. For example, the microphone produces intrinsic noise (e.g., when the dynamic range is too limited). Also, the body tissue surrounding the microphone housing produces various biological noises. Such undesired and unnecessary noises can be very distracting and otherwise problematic. U.S. Patent Publication 20080194953 describes an arrangement wherein the microphone output is not passed along to further signal processing circuitry unless and until the amplitude of the microphone signal exceeds a given threshold value. Thus, an implanted sensing microphone generates an electrical microphone signal representative of acoustic activity in an internal sensing location of a user. A sensing gate, coupled to the microphone and responsive to the microphone signal, has a sensing gate threshold value such that the microphone signal is coupled from the sensing gate to an implanted signal processor when the microphone signal has a magnitude greater than the sensing gate threshold, and the microphone signal is blocked when the microphone signal has a magnitude less than the sensing gate threshold.

Figure 3:
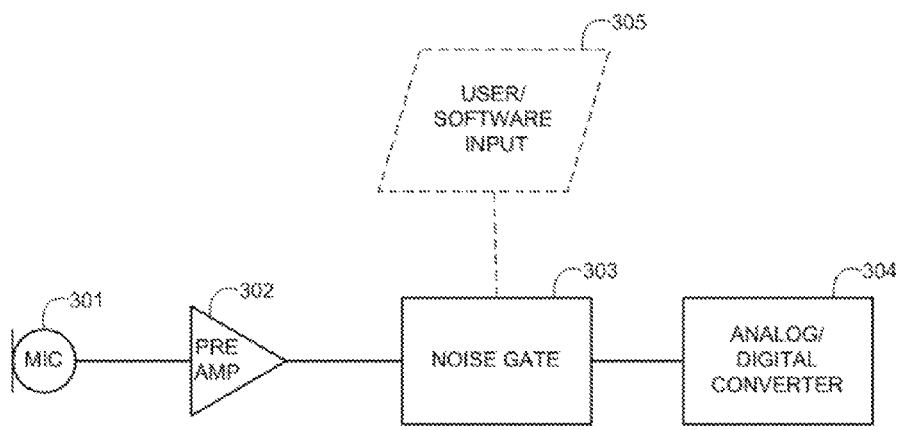
FIG. 3 shows various functional blocks in one specific embodiment.

FIG. 3 in U.S. Patent Publication 20080194953 shows various functional blocks in one specific embodiment. An implanted sensing microphone 301 is located in the housing of an implanted receiver processor 109 just under the skin of the patient user. The sensing microphone senses the nearby acoustic activity and generates a representative electrical microphone signal, which is output to a preamp 302 that linearly amplifies the microphone signal. The preamp 302 couples the amplified microphone signal to the input of sensing gate 303. The sensing gate 303 compares the microphone signal to a sensing gate threshold value. When the microphone signal is less than the threshold, it is blocked by the sensing gate 303. When the microphone signal is greater than the threshold, the sensing gate couples it out the next signal processing stage, in this case, analog/digital converter 304.

Figure 4:
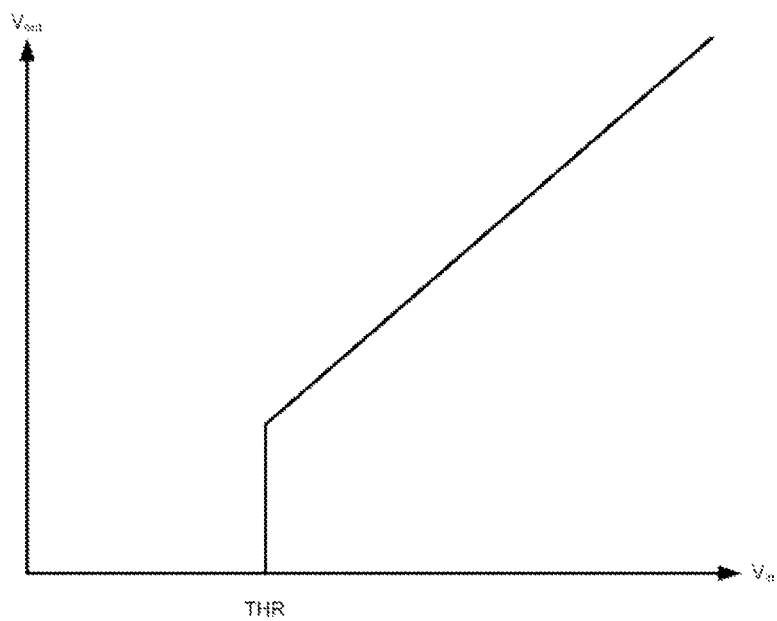
FIG. 4 shows a voltage response curve according to one embodiment.

The functionality of the preamp 302 and the sensing gate 303 may be combined such that signals below the threshold are blocked, and those above the threshold are linearly amplified as shown in the voltage response curve of FIG. 4 of U.S. Patent Publication 20080194953. The sensing gate threshold may also be adjustable, for example, by an optional user/software input 305. And the sensing gate 303 may be digitally implemented so that the input/output curve of FIG. 4 would be implemented as a lookup table in the signal processing blocks. In such an arrangement, the sensing gate 303 would be located after the analog/digital converter 304.

It also may be useful to have a sleep mode that provides a good silence for the user to sleep. In such an arrangement, during the sleep mode the sensing gate threshold may be set to a comparably high value in order to suppress most surrounding noises. Optimally, some loud noises such as the sound of an alarm clock or a smoke detector should exceed threshold so as to be heard by the user.

In addition, most of the energy is lost in energy transfer from the external parts to the implanted components (typically about 60%), so it makes sense to save energy in the front end signal processing. In embodiments of the present invention, the intent is not to save transmission energy as such, but rather to skip the sound signal processing altogether if there is no information of interest that will be processed for the patient. However, it may be favorable to maintain at the same time the transmission of a minimum supply voltage of the implant processor to prevent a total shut down of the implanted electric components. Specifically, embodiments of the present invention introduce an information detection circuit (IDC) as part of the front end sound signal processing circuit. The IDC determines whether the system is in a normal operation mode or it is switched to an energy saving idle mode.

Figure 5:
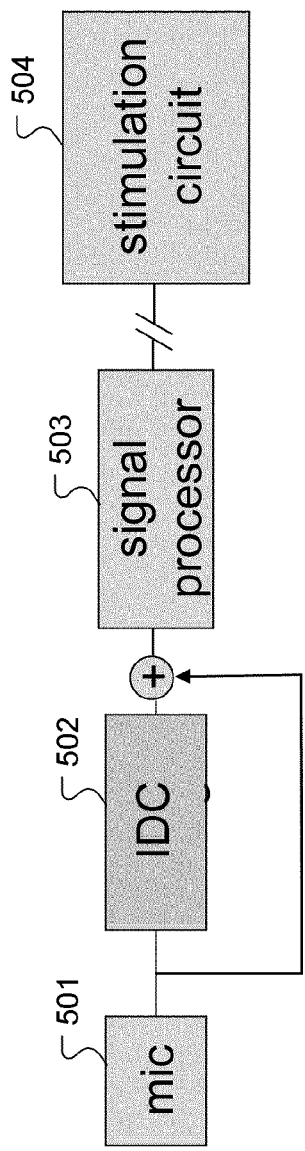
FIG. 5 shows an embodiment of the present invention using an IDC.

For example, FIG. 5 shows a specific example of one embodiment using an IDC. Sensing microphone 501 senses the nearby acoustic activity and generates a representative electrical sound signal. External signal processor 503 compares the sound signal to an information detection threshold value stored by the IDC 502. When the sound signal is less than the threshold, it is blocked by the signal processor 503. When the sound signal is greater than the threshold, the signal processor 503 couples it out the next processing stage, in this case, implanted stimulation circuit 504 that generates stimulation pulses for the implanted electrode contacts.

For example, the information detection threshold of the IDC 502 may be based on detecting the maximum amplitude of the sound signal. If the maximum amplitude of the sound signal is below some (programmable) threshold level, then the IDC 502 switches the signal processor 503 from the normal operational mode to the energy saving idle mode. If the amplitude of the sound signal increases above the threshold, the IDC 502 switches the signal processor 503 back to the normal operational mode. To avoid undesirable oscillations in the state of the system (i.e. if the amplitude of the sound signal stays close to the nominal threshold value) the operational switching of the system between idle mode and normal operational mode may use a hysteresis. For the same reason, it may also be useful to employ a minimum mode time requirement that a given system mode must be active. The hysteresis and/or minimum time period may usefully be programmable, for example, to ensure that the minimal time period is longer than some maximum expected inter-sentence silence break. U.S. Patent Publication 50080194953, incorporated herein by reference, describes an arrangement for reducing noise from a cochlear implant microphone which in some ways is conceptually similar.

Instead of using the signal envelope amplitude as the basis for the IDC threshold decision, other embodiments may be independent from the power spectrum of the sound signal. For example, rather than using signal amplitude or overall energy of the sound signal, some embodiments may be based on using spectral components of the sound signal that are an indicator for speech information.

For example, analysis of an indicator for speech may be based on a Voice Activation Detection (VAD) circuit arrangement as such as those used in other devices like single channel radio transceivers or for IP telefony (see, e.g., http://en.wikipedia.org/wiki/Voice_activity_detection). However, the purpose of a VAD based IDC systems as described herein is different from that in other applications—reduction of the data transfer rate for reduced energy consumption. One advantage of using a VAD-based IDC 502 in combination with the CI sound processor 503 is that much of the functionality needed for a VAD are already realized in the sound processor 503 which is already being used for the system's speech coding strategies.

When the system is in the idle mode, there may be a brief period from the onset of a sound signal containing information such as speech until the IDC has time to switch the signal processor to normal operational mode. The delay period associated with this system mode shift may result in the loss of information present in the sound signal at that time. And this could affect the sound perception performance for the patient user. Various solutions are available to avoid this problem. For example, some embodiments of the present invention provide for a brief storage of the sound signal in a memory device and then send the sound signal on from there with a minimal time shift.

Figure 6:
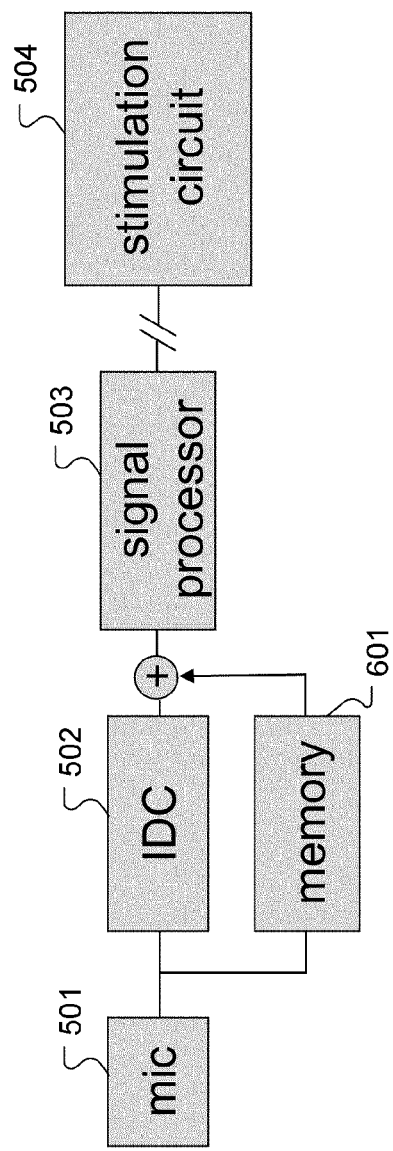
FIG. 6 shows an embodiment similar to FIG. 5 with the addition of a signal memory element.
Figure 7:
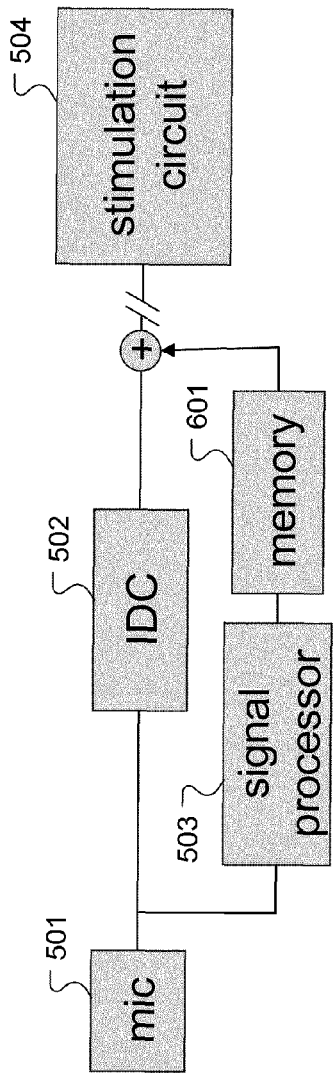
FIG. 7 shows an embodiment where the signal processor precedes in series connection the signal memory and both are in parallel with the IDC.

FIG. 6 shows an example of an embodiment similar to the one in FIG. 5, but where the sound signal from the sensing microphone 501 is briefly stored in a signal memory 601 which is arranged in parallel with the IDC 502 before being passed along to the input of the signal processor 503. FIG. 7 shows an alternative arrangement where the signal processor 503 precedes in series connection the signal memory 601, and both are in parallel with the IDC 502. In this arrangement, rather than storing the sound signal from the sensing microphone 501, it is the implant communications signal from the signal processor 503 that is stored by the signal memory 601. The arrangement in FIG. 6 may be more energy efficient, whereas the arrangement in FIG. 7 may be more memory efficient. The same provisions as discussed above for a hysteresis-based threshold and/or a minimum mode time requirement should be considered.

Figure 8:
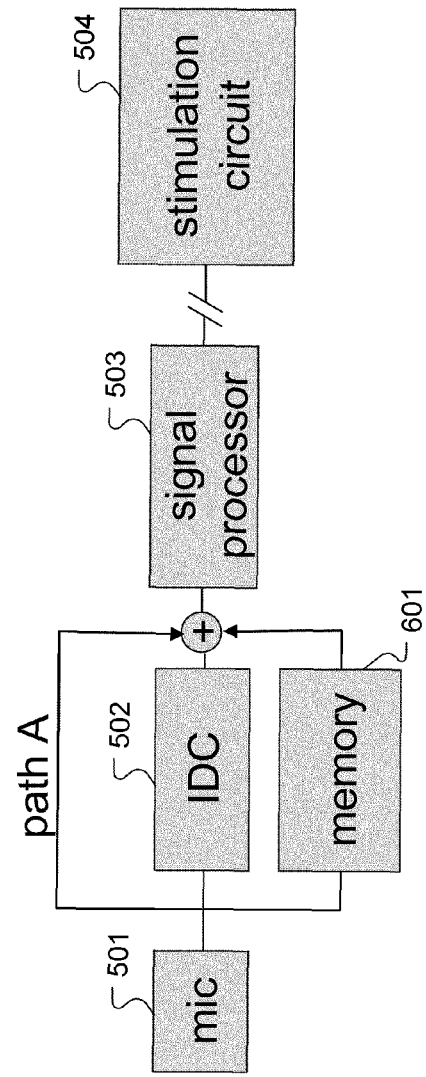
FIG. 8 shows an embodiment similar to FIG. 6 with the addition of a hard wired parallel path.

When using a signal memory 601 as shown in FIGS. 6 and 7, a patient user may perceive a short delay of the speech signal with respect to the lips of a speaker. This is caused by the time required for the electronic processing to occur (such as writing to and reading from memory) and may be up to a few milliseconds. That annoying effect can be minimized by introducing another hard wired connection. FIG. 8 shows an embodiment similar to the one in FIG. 6, with the addition of hard wired path A in parallel with the IDC 502 and the signal memory 601. When the IDC 502 senses speech information present in the microphone signal, speech processor 503 changes from idle mode to operating mode. When the IDC 502 senses and identifies a break in the speech information while in operating mode, the speech processor 503 may select the microphone signal on the hard wired path A for further signal processing rather than the signal passing through signal memory 601. That avoids a memory-based delay between the speech information in the microphone signal and the lip movement of a speaker.

Figure 9:
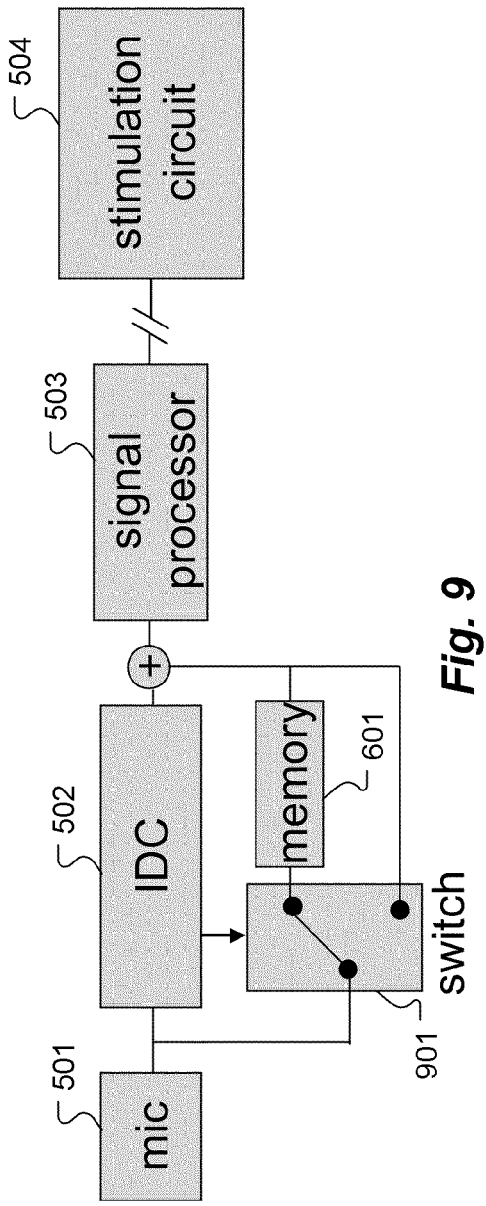
FIG. 9 shows an embodiment which introduces a memory control switch in front of the signal memory.
Figure 10:
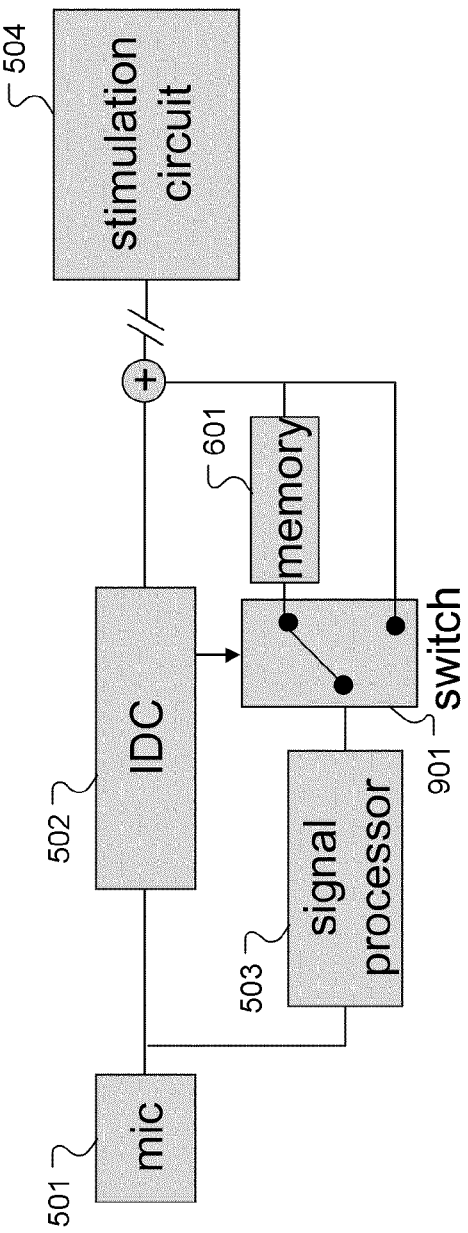
FIG. 10 shows an embodiment similar to FIG. 7 with the signal processor placed in front of the memory control switch.

FIG. 9 shows a different embodiment which introduces a memory control switch 901 in front of signal memory 601. The IDC 502 controls whether the memory control switch 901 switches to the signal path containing signal memory 601 or to the hard wired connection around it. An alternative embodiment shown in FIG. 10 is similar to the system shown in FIG. 7 with the signal processor 503 is placed in front of the memory control switch 901. This arrangement is more memory efficient than the embodiment in FIG. 9.

In any of the embodiments described above, one or more of the electronic components such as signal processor 503 or signal memory 601 may be independently switched off when they are not in use, i.e. during idle mode or when a hard wired path around it is selected. And in partially implantable systems, the transcutaneous energy transfer also may be blocked or reduced during the idle mode. Similarly, in totally implantable hearing systems, energy can be saved by switching off implanted electronic components when they are not required. Therefore it would be advantageous to use the above described arrangements where the signal processor 503 follows behind the IDC 502. Basically, the same considerations apply to partially implantable hearing systems, but there the largest source of energy loss is the transcutaneous transmission path. Therefore, an arrangement as shown in FIGS. 7 and 10 could be acceptable as well.

In totally implantable hearing systems it also could be convenient for the patient users to stimulate their auditory nerve with sub-threshold stimulation pulses or with a tinnitus masking signal during idle mode operation. See, for example, U.S. Patent Publication 50070503536 and U.S. patent application Ser. No. 12/615,731, which are incorporated herein by reference. However, this option may not be available in partially implantable systems because the implanted stimulation circuit 504 may not receive enough energy for stimulation during idle mode, although there may be some abilities for such an option if the capacity of an implanted battery allows. Also for this reason, it is useful that the idle mode operation may be optionally selected by the patient user. Then if it turns out that the patient feels uncomfortable when there is silence during idle mode, he or she can switch IDC function off and avoid using the idle mode.

One advantage of the IDC-based idle mode may be a considerably extended lifetime for the implanted battery. That is, each charge of the implanted battery will last longer due to energy saved during periods of idle mode operation. Moreover, overall battery lifetime should also be extended since the number of charging cycles over time also should be reduced due to the energy savings realized during idle mode operation. One possible disadvantage could be that sound signals that have a spectral sound energy not covered by the IDC would not be processed, for example, alarm sounds.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments also can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A signal processing arrangement for a cochlear implant system comprising:
    a sensing microphone for sensing an acoustic signal to generate a corresponding electrical sound signal;
    an information detection circuit for performing spectral analysis on the sound signal to identify the presence of speech information; and
    a sound signal processing circuit for generating an implant communications signal for the cochlear implant system based on the sound signal, and having an energy saving operational mode controlled based on a hysteresis threshold wherein the implant communications signal is generated only when the information detection circuit identifies that speech information is present in the sound signal.

2. An arrangement according to claim 1, wherein a minimum amount of supply voltage is provided to the implant processor when the information detection circuit identifies that no speech information is present in the sound signal.

3. An arrangement according to claim 1, wherein the hysteresis threshold is software programmable.

4. An arrangement according to claim 1, wherein the hysteresis threshold is user controllable.

5. An arrangement according to claim 1, wherein the arrangement includes a minimum operational time requirement for which the sound signal processing circuit is enabled by the information detection circuit.

6. An arrangement according to claim 1, wherein the information detection circuit includes a voice activation detections (VAD) circuit using a windowed spectral power analysis approach.

7. An arrangement according to claim 1, further comprising:
    a signal delay memory for providing a processing delay to avoid loss of speech information around the time when the information detection circuit initially identifies that speech information is present in the sound signal.

8. An arrangement according to claim 7, wherein the signal delay memory is in parallel with information detection circuit.

9. An arrangement according to claim 8, wherein the sound signal processing circuit is in parallel with the information detection circuit and in series with the signal delay memory.

10. An arrangement according to claim 9, further comprising:
    a memory control switch between the sound signal processing circuit and the signal delay memory for controlling whether the implant communications signal passes through or bypasses the signal delay memory.

11. An arrangement according to claim 8, further comprising:
    a direct signal path in parallel with the information detection circuit and the signal delay memory for coupling the sound signal directly to the sound signal processing circuit without delay.

12. An arrangement according to claim 11, further comprising:
    a memory control switch in series with the direct signal path and the signal delay memory for controlling whether the sound signal passes through the direct signal path or the signal delay memory.

13. A cochlear implant system having a signal processing arrangement according to any of claims 1, 2, and 3-12.

14. A method for signal processing in a cochlear implant system comprising:
    sensing an acoustic signal with a sensing microphone to generate a corresponding electrical sound signal;
    performing spectral analysis on the sound signal with an information detection circuit to identify the presence of speech information; and
    generating an implant communications signal for the cochlear implant system with a sound signal processing circuit in an energy saving operational mode controlled based on a hysteresis threshold based on the sound signal only when the information detection circuit identifies that speech information is present in the sound signal.

15. A method according to claim 14, wherein the hysteresis threshold is software programmable.

16. A method according to claim 14, wherein the hysteresis threshold is user controllable.

17. A method according to claim 14, wherein generating the implant communications signal satisfies a minimum operational time requirement for which the sound signal processing circuit is enabled by the information detection circuit.

18. A method according to claim 14, wherein the information detection circuit includes a voice activation detections (VAD) circuit using a windowed spectral power analysis approach.

19. A method according to claim 14, further comprising:
providing a processing delay with a signal delay memory to avoid loss of speech information around the time when the information detection circuit initially identifies that speech information is present in the sound signal.

20. A method according to claim 19, wherein the signal delay memory is in parallel with information detection circuit.

21. A method according to claim 20, wherein the sound signal processing circuit is in parallel with the information detection circuit and in series with the signal delay memory.

22. A method according to claim 21, further comprising:
controlling with a memory control switch whether the implant communications signal passes through or bypasses the signal delay memory.

23. A method according to claim 21, further comprising:
coupling the sound signal directly to the sound signal processing circuit without delay.

24. A method according to claim 23, further comprising:
controlling with a memory control switch whether the sound signal passes through the direct signal path or the signal delay memory.

25. A method according to claim 14, further comprising:
providing a minimum amount of supply voltage to the implant processor when the information detection circuit identifies that no speech information is present in the sound signal.

* * * * *